(12) United States Patent
Gurjar et al.

(10) Patent No.: US 7,109,353 B2
(45) Date of Patent: Sep. 19, 2006

(54) PROCESS FOR PREPARING 5,6-DIHYDRO-4-(S)-(ETHYLAMINO)-6-(S) METHYL-4H-THIENO[2,3B]THIOPYRAN-2-SULPHONAMIDE-7,7-DIOXIDE HCL

(75) Inventors: Mukund Keshao Gurjar, Pune (IN); Madhusudan Nagorao Deshmukh, Pune (IN); Vincent Paul, Pune (IN); Venkatasubramaniam Radhakrishnan Tarur, Mumbai (IN); Dhananjay Govind Sathe, Mumbai (IN); Santosh Pratap Pardeshi, Mumbai (IN); Sanjay Janardhan Naik, Mumbai (IN); Tushar Anil Naik, Mumbai (IN)

(73) Assignee: Council of Scientific and Industrial Research, New Delhi (IN)

( * ) Notice: Subject to any disclaimer, the term of this patent is extended or adjusted under 35 U.S.C. 154(b) by 134 days.

(21) Appl. No.: 11/024,029

(22) Filed: Dec. 28, 2004

(65) Prior Publication Data
US 2006/0142595 A1    Jun. 29, 2006

(51) Int. Cl.
*C07D 335/04* (2006.01)
(52) U.S. Cl. ....................................... 549/23
(58) Field of Classification Search ............ 549/23
See application file for complete search history.

(56) References Cited

U.S. PATENT DOCUMENTS 4,797,413 A * 1/1989 Baldwin et al. ............ 514/432
4,863,922 A * 9/1989 Baldwin et al. .......... 514/232.5
5,688,968 A * 11/1997 Blacklock et al. ............ 549/23
7,030,250 B1 * 4/2006 Losada et al. ................ 549/23

FOREIGN PATENT DOCUMENTS

| EP | 0 296 879 | 12/1988 |
| EP | 0 453 288 | 10/1991 |
| EP | 0 617 037 | 9/1994 |

* cited by examiner

Primary Examiner—Deborah C. Lambkin
(74) Attorney, Agent, or Firm—Ladas and Parry LLP

(57) ABSTRACT

The present invention relates to an improved process for the preparation of 5,6-dihydro-4-(S)-(ethylamino)-6-(S)methyl-4H-thieno[2,3b]thiopyran-2-sulphonamide-7,7-dioxide hydrochloride of formula (I) commonly known as Dorzolamide Hydrochloride useful as an agent to reduce intraoccular pressure by inhibiting carbonic anhydrase enzyme

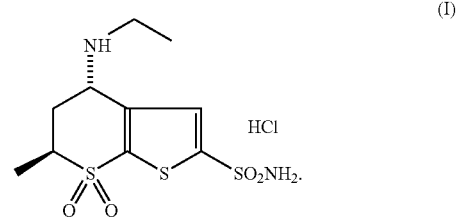

34 Claims, No Drawings

PROCESS FOR PREPARING 5,6-DIHYDRO-4-(S)-(ETHYLAMINO)-6-(S) METHYL-4H-THIENO[2,3B]THIOPYRAN-2-SULPHONAMIDE-7,7-DIOXIDE HCL

FIELD OF THE INVENTION

The present invention relates to an improved process for the preparation of 5,6-dihydro-4-(S)-ethylamino)-6-(S)methyl-4H-thieno[2,3b]thiopyran-2-sulphonamide-7,7-dioxide hydrochloride commonly known as Dorzolamide Hydrochloride. This compound is described in U.S. Pat. No. 4,797,413 as an agent to reduce intraoccular pressure by inhibiting carbonic anhydrase enzyme.

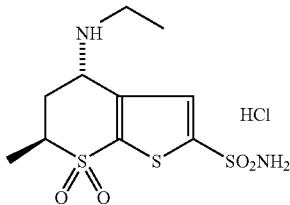

(I)

BACKGROUND OF THE INVENTION

A process for the preparation of Dorzolamide Hydrochloride and its derivatives is known. U.S. Pat. No. 5,688,968 describes preparation of Dorzolamide HCl starting from chiral 5,6-dihydro-4-(S)-hydroxy-6-(S)-methyl-4H-thiopyran-7,7-dioxide, as depicted in scheme 1:

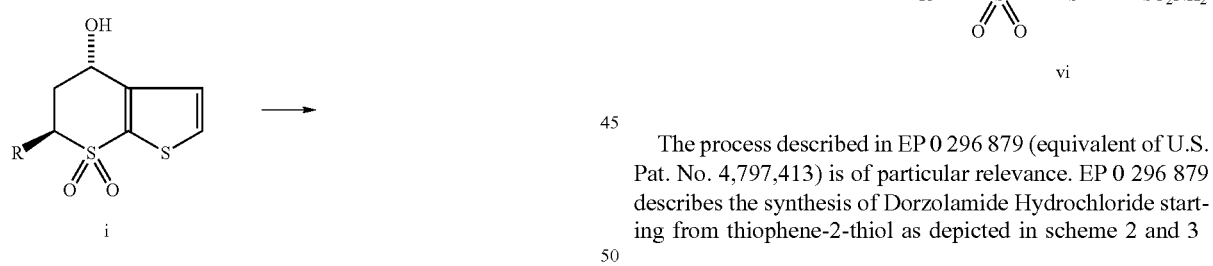

The process described in EP 0 296 879 (equivalent of U.S. Pat. No. 4,797,413) is of particular relevance. EP 0 296 879 describes the synthesis of Dorzolamide Hydrochloride starting from thiophene-2-thiol as depicted in scheme 2 and 3

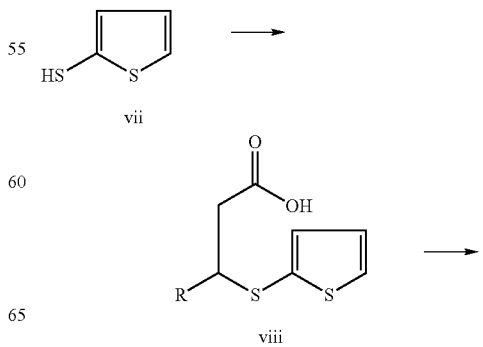

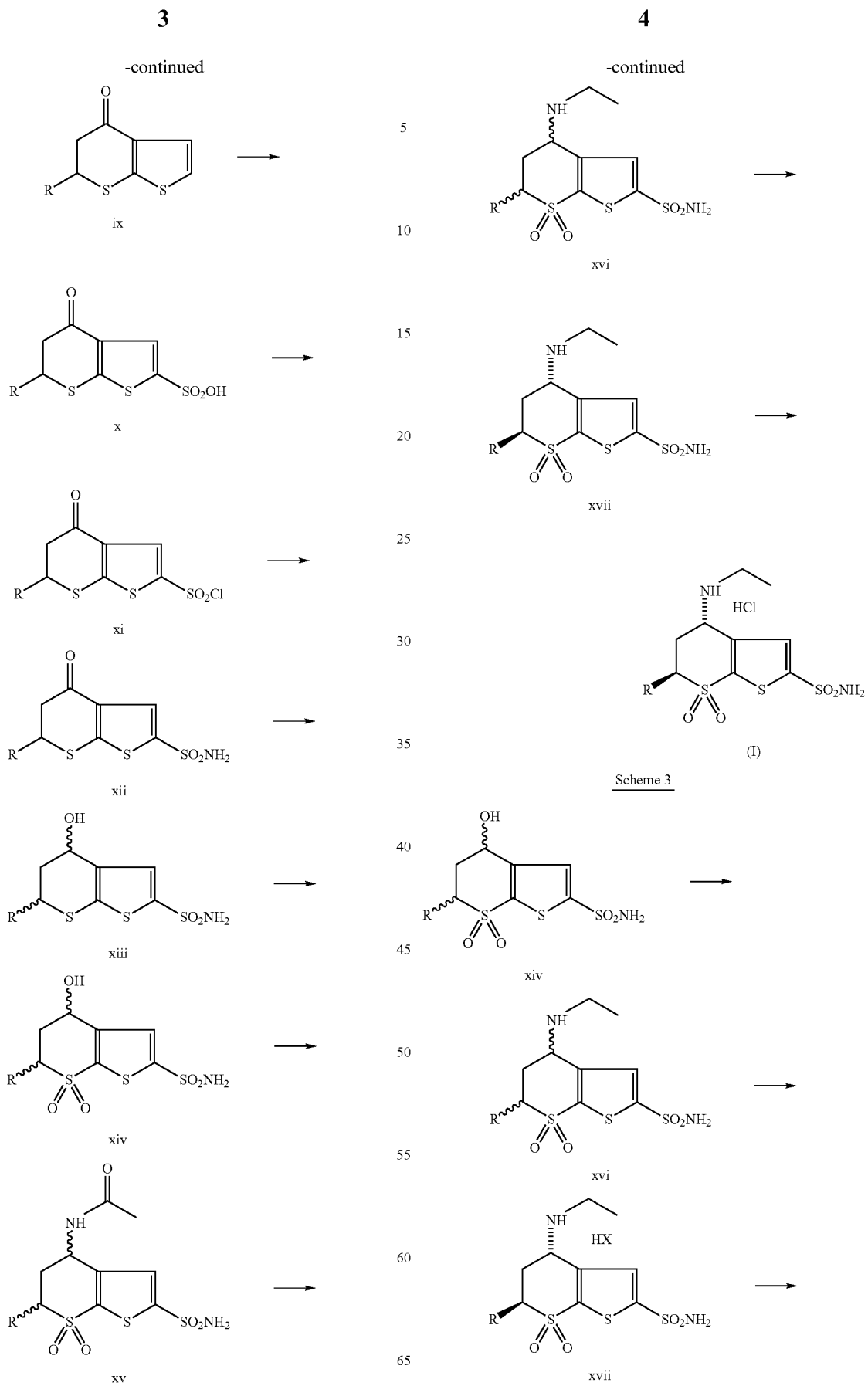

-continued

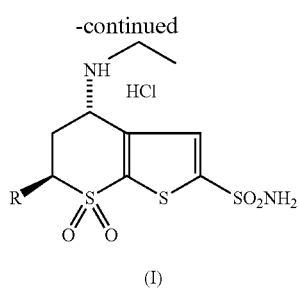

(I)

The process described in EP 0,296,879 (scheme 2) has the following disadvantages: (a) The starting material Thiophene-2-thiol is unstable and undergoes oxidation to form disulfide, leading to lower yield of viii; (b) the yield of sulfonamide (xii) from sulphonic acid (x) is very poor (35%) and requires use of 18-crown-6 ether, which is expensive; (c) oxidation of alcohol (xiii) to sulfone is carried out using oxone which is expensive and hazardous; and separation of cis/trans isomer is done by column chromatography which is industrially inconvenient.

OBJECTIVE OF THE INVENTION

The object of present invention is to provide an improved process for commercial manufacture of 5,6-dihydro-4-(S)-(ethylamino)-6-(S)methyl-4H-thieno[2,3b]thiopyran-2-sulphonamide-7,7-dioxide hydrochloride commonly known as Dorzolamide Hydrochloride starting from stable 2-bromo thiophene.

Another object of the invention is to provide an improved process for Dorzolamide hydrochloride preparation, which is less time consuming involving fewer steps and increases the product efficiency.

Another object of the invention is to provide a process for Dorzolamide hydrochloride manufacture, which avoids use of expensive catalyst.

Another object of the invention is to provide a process for Dorzolamide hydrochloride manufacture, which avoids the use of expensive reagents.

Another object of the invention is to provide a process for Dorzolamide hydrochloride manufacture, which is industrially feasible.

SUMMARY OF THE INVENTION

Accordingly, the present invention provides a process for preparing 5,6-dihydro-4-(S)-(ethylamino)-6-(S)methyl-4H-thieno[2,3b]thiopyran-2-sulphonamide-7,7-dioxide hydrochloride of formula (I),

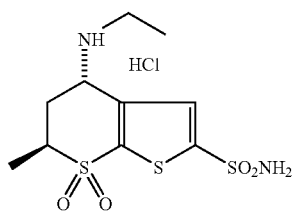

(I)

the process comprising (a) react compound of formula II wherein X is halo, with magnesium metal and treating the generated Grignard reagent in a solvent in situ with sulfur, triethyl amine hydrochloride, crotonic acid and suitable base to obtain compound of formula III,

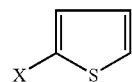

II

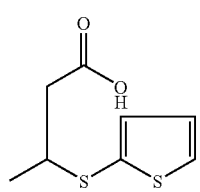

III (b) reacting compound of formula III with a chlorinating agent to obtain a acid chloride, followed by subjecting the acid chloride to cyclisation in the presence of a Lewis acid to obtain a compound of formula IV;

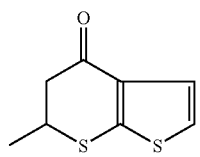

IV (c) reacting compound of formula IV with a mixture of chlorosulphonic acid and a chlorinating agent to form a sulphonylchloride of formula XX, extracting the sulphonylchloride in a chlorinated solvent, washing with water, drying and evaporating the chlorinated solvent to obtain compound of formula V;

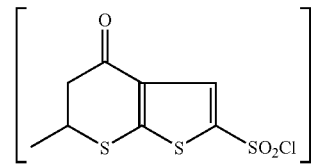

XX

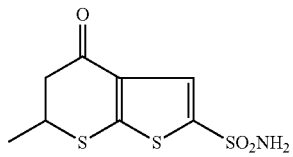

V (d) reducing compound of formula V to obtain compound of formula VI;

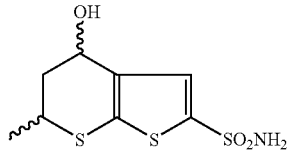

VI (e) oxidising compound of formula VI to obtain compound of formula VII;

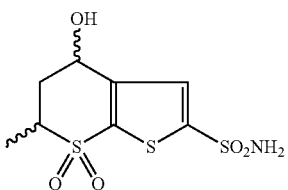

VII (f) subjecting compound of formula VII to a Ritter reaction to obtain compound of formula VIII

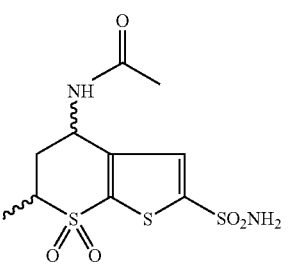

VIII (g) reducing compound of formula VIII to obtain compound of formula IX

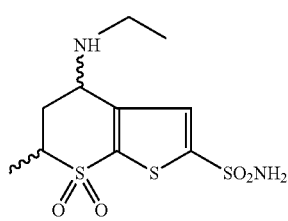

IX (h) converting compound of formula IX to acid addition salt thereof of formula XXI and recrystallizing enriched salt from the solvent and then converting salt of formula XXI to compound of formula X

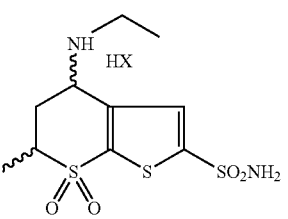

XXI

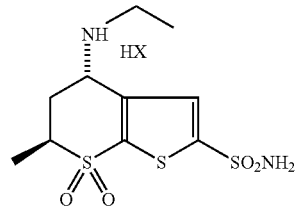

X (i) resolving compound of formula X into compound of formula I.

In one embodiment of the invention, in step (a), the organic solvent is selected from the group consisting of ethers, cyclic ethers and aromatic hydrocarbon.

In another embodiment of the invention, the organic solvent used in step (a) is tetrahydrofuran.

In yet another embodiment of the invention, step (a) is carried out in the presence of a base selected from the group consisting of organic alkylamine and pyridine.

In a further embodiment of the invention, the base is trialkyl amine.

In a preferred embodiment the base is triethyl amine.

In another embodiment of the invention, in compound of formula II, X is a halo selected from the group consisting of Cl, Br and I.

In another embodiment of the invention, step (a) is carried out at a temperature in the range of 0° C. to 70° C.

In another embodiment of the invention, in step (b), the organic solvent is an aprotic non-polar solvent.

In another embodiment of the invention, the aprotic non-polar solvent used is a chlorinated solvent such as MDC.

In another embodiment of the invention, the Lewis acid is selected from the group consisting of $AlCl_3$, $ZnCl_2$ and $SnCl_4$ and more preferably $SnCl_4$.

In another embodiment of the invention, sulfonyl chloride of formula XX is dissolved in an organic solvent selected from the group consisting of ether and ketone.

In a further embodiment of the invention, the organic solvent is tetrahydrofuran.

In another embodiment of the invention, the sulfonyl chloride of formula XX is dissolved in an organic sovlent and then treated with ammonia followed by chlorination with a chlorinating agent selected from the group consisting of $POCl_3$, $PCl_5$, $PCl_3$, $SOCl_3$ and more preferably $SOCl_2$ and in the presence of a chlorination solvent selected from the group consisting of $CHCl_3$, MDC, and EDC, preferably MDC.

In another embodiment of the invention, in step (d) reduction is effected using sodium borohydride in the presence of a solvent and at a temperature in the range of 0° C. to 40° C.

In a further embodiment of the invention, the solvent is a lower aliphatic alcohol and more preferably methanol.

In another embodiment of the invention, in step (e) compound of formula VI is oxidised with sodium perborate in presence of acetic acid at 20° C. to 70° C.

In another embodiment of the invention, in step (f) the Ritter reaction of compound of formula VII is effected in a strong acid with acetonitrile at 10° C. to 40° C.

In a further embodiment of the invention, the strong acid is selected from the group consist of sulfuric acid and a mixture of concentrated sulfuric acid and forming sulfuric acid.

In another embodiment of the invention, in step (g), reduction is effected using borane dimethylsulfide complex in an organic solvent selected from ether and cyclic ether.

In a further embodiment of the invention, the organic solvent used in step (g) is tetrahydrofuran.

In another embodiment of the invention, in step (h), the organic solvent is selected from the group consisting of a ketone, an ester, a dipolar aprotic solvent, lower aliphatic alcohol, aliphatic hydrocarbon and aromatic hydrocarbon.

In a further embodiment of the invention, the ester is ethyl acetate.

In a further embodiment of the invention, the acid used for salt formation in step (h) is a mineral acid selected from the group consisting of HCl, $H_2SO_4$, $HNO_3$, and HBr more preferably HCl dissolved in a lower aliphatic alcohol.

In a further embodiment of the invention, the acid used for salt formation in step (h) is ethanolic HCl.

In another embodiment of the invention, the organic solvent used for recrystallization is selected from the group consisting of a ketone, an ester, a dipolar aprotic solvent, lower aliphatic alcohol, aliphatic hydrocarbon or aromatic hydrocarbon, preferably an ester, lower aliphatic alcohol or mixture thereof, more preferably ethyl acetate, ethanol or mixture thereof.

In a further embodiment of the invention, the compound of formula X is rsolved using di-p-toluyl-L-tartarate and di-p-toluyl-D-tartarate.

DETAILED DESCRIPTION OF THE INVENTION

The invention provides a process for preparing 5,6-dihydro-4-(S)-(ethylamino)-6-(S)methyl-4H-thieno[2,3b]thiopyran-2-sulphonamide-7,7-dioxide hydrochloride of formula (I), comprising of nine steps, as depicted in scheme 4 below:

Scheme 4

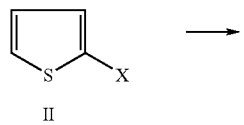

II

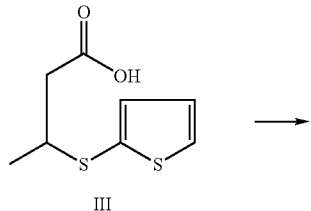

III

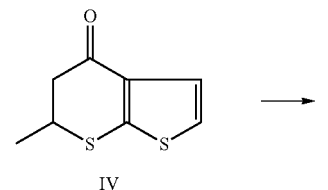

IV

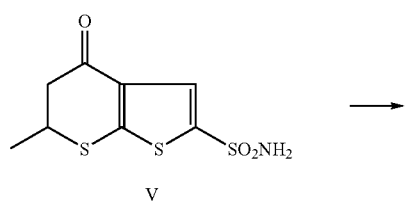

V

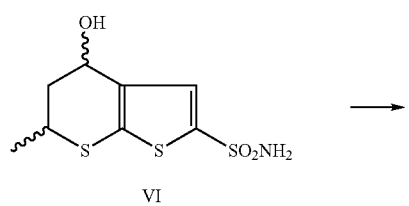

VI

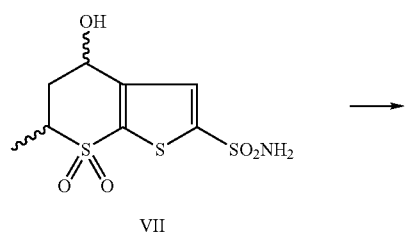

VII

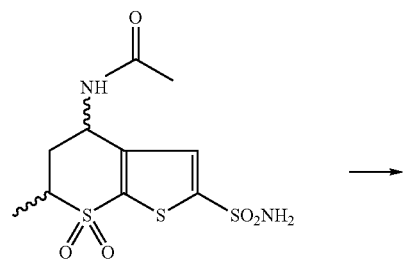

VIII

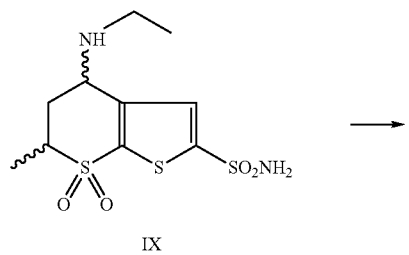

IX

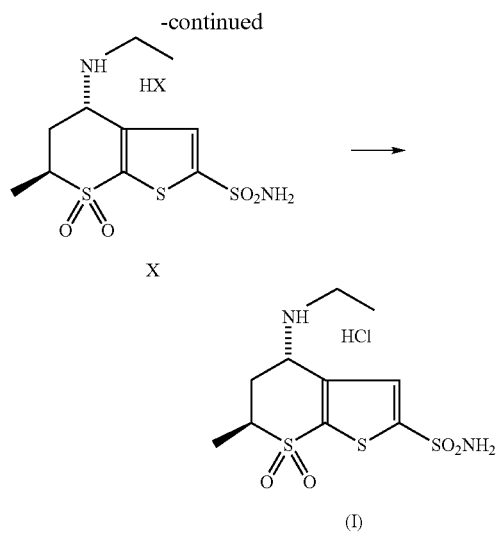

Step I:

Preparation of compound of formula III by reacting compound of formula II with magnesium metal followed by treatment of thus generated Grignard reagent in a solvent in situ with sulfur, triethyl amine hydrochloride, crotonic acid and suitable base at 0° C. to 70° C. as shown in scheme 5, Scheme 5

X of formula II is a halo —Cl, —Br, —I preferably —Br.

The organic solvents are ethers, cyclic ethers and aromatic hydrocarbon but preferably cyclic ethers and sore preferably THF. The base is an organic alkylamine or pyridine, preferably trialkyl amine and more preferably triethyl amine.

Step II:

Preparation of compound of formula IV by reacting compound of formula III with chlorinating agent followed by cyclisation of acid chloride of formula XIX generated in-situ in presence of Lewis acid in a solvent at 0° C. to 40° C. as shown in scheme 6.

Scheme 6

The organic solvents are aprotic non-polar solvents, preferably chlorinated solvents and more preferably MDC. Lewis acids are $AlCl_3$, $ZnCl_2$, $SnCl_4$ and more preferably $SnCl_4$.

Step III:

Preparation of compound of formula V by reacting compound of formula IV with mixture of chlorosulphonic acid and chlorinating agent at −10° C. to 10° C., extracting thus formed sulphonylchloride of formula XX in a chlorinated solvent, washing with water, drying and evaporating the chlorinated solvent. Dissolving the sulfonyl chloride of formula XX in suitable organic solvents followed by treatment with ammonia as shown in scheme 7

Scheme 7

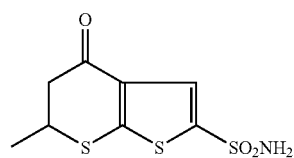

The chlorination agent is selected from $POCl_3$, $PCl_5$, $PCl_3$, $SOCl_2$ and more preferably $SOCl_2$. Chlorination solvents are preferably selected from $CHCl_3$, MDC, and EDC, more preferably MDC. The organic solvent for dissolving sulfonyl chloride is an ether or a ketone, preferably other and more preferably THF.

Step IV:

Preparation of compound of formula VI by reducing compound of formula V with sodium borohydride in presence of solvent at 0° C. to 40° C. as shown in scheme 8.

Scheme 8

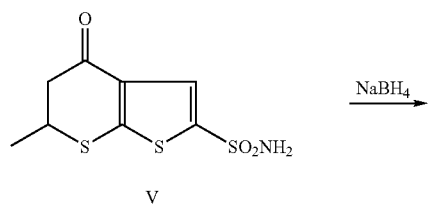

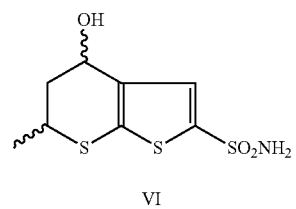

The organic solvent is lower aliphatic alcohol and more preferably methanol.

Step V:

Preparation of compound of formula VII by oxidizing compound of formula VI with sodium perborate in presence of acetic acid at 20° C. to 70° C. as shown in scheme 9.

Scheme 9

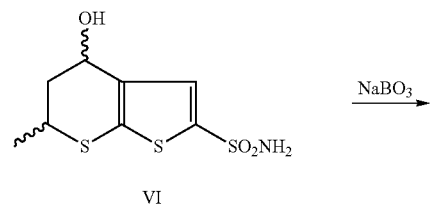

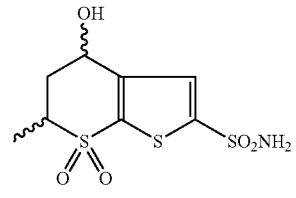

Step VI:

Preparation of compound of formula VIII by Ritter reaction of compound of formula VII in strong acid with acetonitrile at 10° C. to 40° C. as shown in scheme 10.

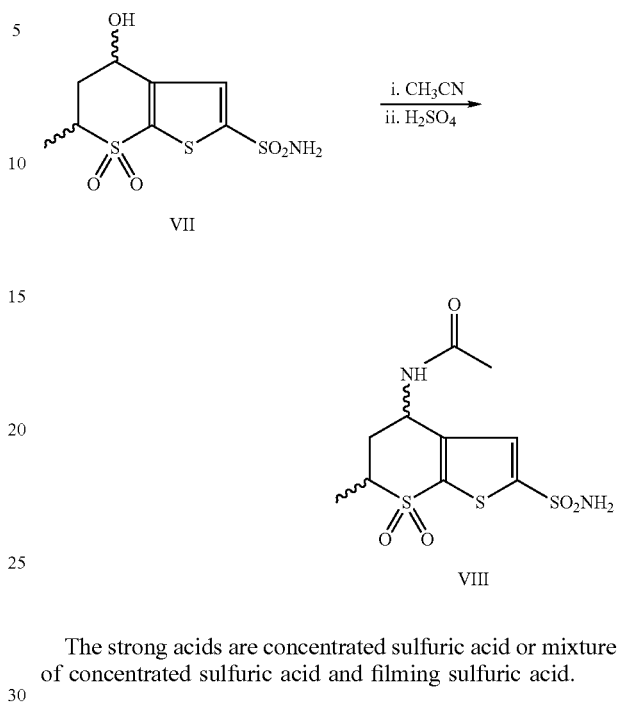

The strong acids are concentrated sulfuric acid or mixture of concentrated sulfuric acid and filming sulfuric acid.

Step VII:

Preparation of compound of formula IX by reducing compound of formula VIII with borane dimethylsulfide complex in organic solvents. As shown in scheme 11

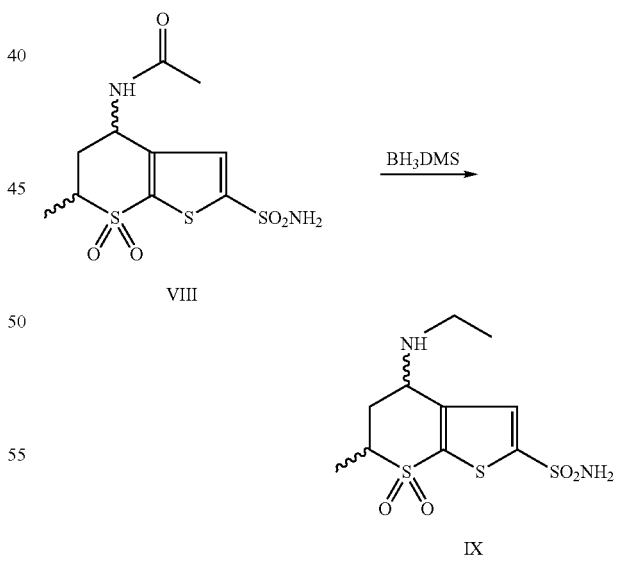

The organic solvents are ethers, cyclic ethers, preferably cyclic ethers and more preferably THF.

Step VIII:

Preparation of compound of formula X by converting the compound of formula IX to its acid addition salt in a solvent followed by recrystallisation of the enriched salt from an organic solvent or a mixture of solvents as shown in scheme 12. The organic solvent is a ketone, an ester, a dipolar aprotic solvent, lower aliphatic alcohol aliphatic hydrocarbon or aromatic hydrocarbon, preferably an ester and more preferably ethyl acetate. The acid used for salt formation is a mineral acid like HCl, $H_2SO_4$, $HNO_3$, HBr more preferably HCl dissolved in lower aliphatic alcohol preferably ethanol. The acid used for salt formation is most preferably ethanolic HCl. The organic solvent for recrystallization is a ketone, an ester, a dipolar aprotic solvent, lower aliphatic alcohol, aliphatic hydrocarbon or aromatic hydrocarbon, preferably an ester, lower aliphatic alcohol or mixture thereof, more preferably ethyl acetate, ethanol or mixture thereof.

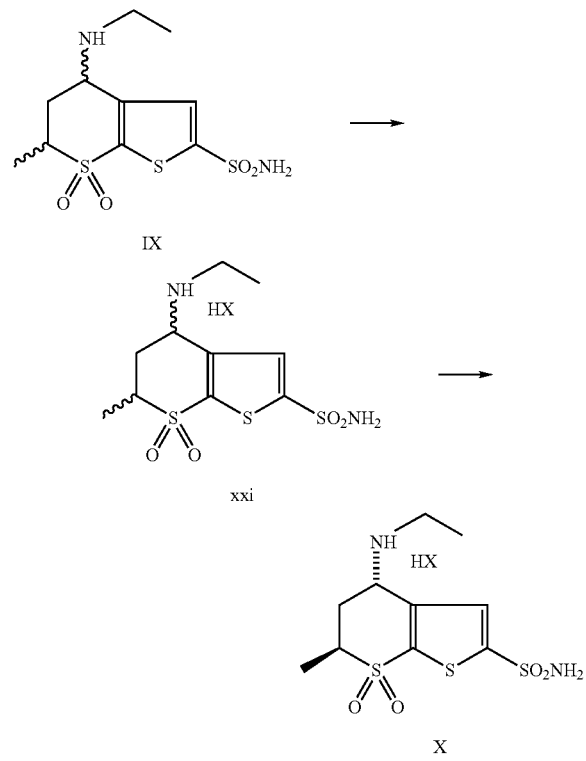

Step IX:

Preparation of compound of formula I by resolution of compound of formula X using di-p-toluyl-L-tartarate and di-p-toluyl-D-tartarate.

The process of manufacturing Dorzolamide hydrochloride by the present invention comprises use of 2-bromo thiophene as a stating material avoiding use of unstable thiophene-2-thiol. The process of the said invention requires less number of steps since sulfonamide of formula IV is prepared directly from compound of formula III avoiding isolation of sulfonic acid X. This eliminates the use of an expensive catalyst. The process of invention uses cheap, commercially available sodium perborate as an oxidizing agent, thus making the process more economical. The process of the said invention makes use of hydrochloride salt formation as a means to separate cis:trans isomer thus avoiding industrially cumbersome column chromatography.

EXPERIMENTAL

Example 1

Preparation of (RS) 3-(2-mercaptothiophene)butanioc acid (III)

To a mechanical stirred mite of magnesium turnings (20 gm, 0.833 moles) in THF (700 ml), crystal of iodine and 2-bromo thiophene (II) (5.0 gm 0.0305 mole) were added to initiate reaction. Once reaction was initiated, 2-bromo thiophene (95 gm 0.58 mole) was added to maintain reflux which was then continued for 2 hrs then cooled to 45° C. Sulfur (19.66 gm, 0.614 mole) was then added maintaining temp. below 50° C. and stirring continued for 2 hrs. Triethyl amine hydrochloride (84 gm, 0.611 mole) was then added at 45° C. and stirring continued for 1 hrs. A mixture of triethyl amine (80 gm, 0.79 mole) and crotonic acid (63 gm, 0.733 mole) in THF (200 ml) was then added at 45° C. The mixture was refluxed for 18 to 20 hrs. pH was adjusted to 2 to 2.5 by 6 N HCl at 0° to 15° C. The compound of formula (III) was extracted with MDC and concentrated to dryness to gave title compound (123 gm, 100%).

$^1$H NMR (CDCl3) δ 1.35 (d, 3H, J=6.9 Hz, $CH_3$) 2.48 (dd, 1H, J=8.0 J=16.1 Hz,$CH_2$) 2.77 (dd, 1H, J=6.4 J=16.1 Hz, $CH_2$) 3.36–3.42 (m, 1H,CH) 7.03 (dd, 1H, J=3.4 J=5.3 Hz, 3-H) 7.20 (dd, 1H, J=1.2 J=3.4 Hz, 4-H) 7.43 (dd, 1H, J=1.2 Hz, J=5.3 Hz, 2-H)

Example 2

Preparation of 5,6 dihydro-4H-6-methylthieno[2,3-b]thi-opyran-4-one (IV)

To a solution of product from example 1 (123 gm 0.609 mole) in MDC (1845 m) and DMF (10 ml) thionyl chloride (54.35 ml, 0.73 mole) was added dropwise and mixture stirred at reflux temperature of 37 to 40° C. for 2 hrs. The mixture was cooled to −10° C. and a solution of $SnCl_4$ (39.12 ml, 0.33 moles) in MDC was added dropwise maintaining temperature below 0° C. The reaction was stirred at 0° C. for 1 hr, and water (500 ml) was then added dropwise while maintaining temperature below 10° C. The layers were separated. The aqueous phase was extracted with MDC and organic layers were washed with water followed by saturated bicarbonate solution, finally with brine. MDC layer was then stirred with silica gel (100 gm), filtered and washed by MDC. Organic layer was dried with anhydrous sodium sulphate. Finally organic layer was concentrated completely to get title compound (91 gm, 81.1%)

$^1$H NMR (CDCl3) δ 1.48 (d, 3H, J=6.9 Hz, $CH_3$) 2.69 (dd, 1H, J=11.4 J=16.8 Hz, $CH_2$) 2.88 (dd,1H, J=3.2 J=16.8 Hz, $CH_2$) 3.80 (t,1H, CH) 7.01 (d,1H, J=5.5 Hz, 3-H)7.46 (d, 1H, J=5.5 Hz, 2-H)

Example 3

Preparation of 5,6 dihydro-4H-6-methylthieno[2,3-b]thi-opyran-4-one-2-sulfonamide (V)

To stirred solution of chlorosulphonic acid (196.9 ml, 2.96 mole), thionyl chloride (71.67 ml, 0.987 mole) was added slowly at temperature 0° C. to 10° C. The mixture was stirred at a temperature of 30° C. to 32° C. for 3 hrs and then cooled to 0° C. Compound prepared in Example 2 (91 gm, 0.494 Mole) was slowly added at temperature of 0° C. to 5° C. The mixture was then stirred at temperature of 0 to 5° C. for 1 hr and the temperature then raised to 25 to 30° C. and maintained for 5 to 10 hrs. MDC (1000 ml) was then added and the reaction mass was quenched using 700 gm of ice below temperature of 20° C. The lower organic layer was separated. The aqueous layer was extracted with MDC and mixed to main organic layer which is washed with chilled water. The organic layer was concentrated to get a sticky mass (130 gm) which was then dissolved in THF (100 ml), to which was added to (150 ml) chilled liquor ammonia. This was stirred for 2 hrs and ice water (2000 ml) added. This was further stirred for 3 hrs and filtered and washed with water, and dried to get title compound (V) (65 gin 50%).

$^1$H NMR (DMSO d-6) δ 1.51 (d, 3H, J=6.9 Hz, CH$_3$) 2.70 (dd, 1H, J=11.4 J=16.8 Hz, CH$_2$) 2.93 (dd, 1H, J=3.2 J=16.8 Hz,CH$_2$) 3.80–4.0 (bm, 1H, CH) 4.62–4.80 (bm, 1H, CH) 7.32 (bs, 2H, NH$_2$) 7.84 (d, 1H, J=5.5 Hz, 3-H)

Example 4

Preparation of 5,6 dihydro-4H-4-hydroxy-6-methylthieno[2,3-b]thiopyran-2-sulfonamide (VI)

To a suspension of product from example 3 (65 gm, 0.247 mole) in methanol (455 ml) sodium borohydride (7.03 gm, 0.185 mole) was added and the resulting mixture stirred for 2 hrs at 25 to 30° C. Methanol was concentrated from reaction mixture to get a sticky mass. Water (1000 ml) was added to the sticky mass and the mixture stirred for 0.5 hrs and the pH adjusted to 6.5 to 7.0 by acetic acid. Stirring was then done 1 hrs at 20 to 25° C. The product obtained was filtered and washed with water. The cake was sucked to remove as much water as possible, and dried to get title compound (64.4 gm, 99%).

Example 5

Preparation of 5,6 dihydro-4H-4-hydroxy-6-methylthieno[2,3-b]thiopyran-2-sulfonamide-7,7 dioxide (VII)

To a suspension of product from example 4 (64.4 gm, 0.242 mole) in Acetic acid (320 ml) sodium perborate (83.48 gm, 0.545 mole) was added and resulting mixture stirred for 1 hr at 25 to 30° C., then heated to attain temperature 60 to 65° C. and maintained for 3 hrs. Acetic acid was concentrated from reaction mixture to get a sticky mass, which was dissolved in water (400 ml). Product was extracted with ethyl acetate. Organic layer was concentrated to keep inside volume 100 ml and then cooled to 0 to 5° C. and stirred for 2 hrs. The product was filtered and washed with chilled ethyl acetate. The cake was sucked to remove as much ethyl acetate as possible, and dried to get title compound (55 gm, 76.27%).

$^1$H NMR (DMSO d-6) δ 1.49 (d,3H,CH$_3$) 2.42 (m,2H, CH$_2$) 3.55 (m,1H, 6-H) 4.60–4.90 (m,1H, 4-H) 7.51 (bs,2H, NH$_2$) 7.69 (bs,1H, 3-H)

Example 6

Preparation of 5,6 dihydro-4H-4-acetylamino-6-methylthieno[2,3-b]thiopyran-2-sulfonamide-7,7 dioxide (VIII)

A solution of product from example 5 (55 gm, 0.185 mole) in acetonitrile (715 ml) was cooled to 0 to 5° C. and sulfuric acid (167.5 ml, 3.144 mole) added dropwise maintaining temperature 0 to 5° C. The temperature was allowed to rise to 25 to 30° C. The mixture was stirred for 25 to 27 hrs. The reaction mixture was added to mixture of water and ethyl acetate below 5° C. and pH of reaction mixture was adjusted to 7.5 by 50% solution of sodium hydroxide. The sodium sulphate salt was filtered and washed with ethyl acetate. The organic layer was separated. Aqueous layer was extracted with ethyl acetate. The organic layer was concentrated to get sticky mass as title compound (VII) (50 gm. 91.6%).

$^1$H NMR (DMSO d-6) δ 1.47(d, 3H, CH$_3$) 1.96 & 2.01 (s,3H each, COCH$_3$) 2.30–2.60 (m,2H, CH$_2$) 3.70–3.85 (m,1H, CH) 5.20–5.30 (m,1H, CH) 7.44 & 7.88 (s, 2H, NH$_2$) 7.59 (s, 1H, 3-H)

Example 7

Preparation of 5,6 dihydro-4H-4-ethylamino-6-methylthieno[2,3-b]thiopyran-2-sulfonamide-7,7 dioxide (IX)

To a solution of borane dimethyl sulfide complex (52.59 ml, 0.546 mole) and THF 108 ml) product from example 6 (50 gm, 0.148 mole) in THF (80 mole) was added at 0 to 5° C. The temperature was allowed to rise 25 to 30° C. and mixture stirred for 10 hrs. The reaction mite was added to 1 N sulfuric acid (190 ml) at 0 to 5° C. and stirred for 1 hr. pH was adjusted to 7 with 50% sodium hydroxide solution, and stirred for 1 hr and then product extracted with ethyl acetate. Ethyl acetate layer was concentrated to get sticky mass as title compound (IX) (39.5 gm, 82.41%).

Example 8

Preparation of Trans 5,6 dihydro-4H-4-ethylamino-6-methylthieno[2,3-b]thiopyran-2-sulfonamide-7,7 dioxide (X)

A solution of product from example 7 (39.5 gm, 0.132 mole) in ethyl acetate (426 ml) was cooled to 0 to 5° C. and ethanolic HCl (20 ml) was added and stirred for 3 hrs at 0 to 5° C. The product was precipitated out, filtered and washed with chilled ethyl acetate. The cake was sucked to remove as much ethyl acetate as possible, and dried to get compound (21 gm) The product was suspended into ethyl acetate (210 ml), refluxed for 1 hr, then cooled to 10° C. The product was filtered and washed with chilled ethyl acetate. The cake was sucked to remove as much ethyl acetate as possible, and dried to hydrochloride salt of title compound (18 gm). The salt was then treated with saturated solution of sodium bicarbonate and mixture extracted with ethyl acetate. The organic extract were dried, filtered and concentrated to dryness to yield title compound (X) (15 gm, 37.98%).

Example 9

Preparation of 5,6 dihydro-4H-4-(S)-ethylamino-6-(S)-methylthieno[2,3-b]thiopyran-2-sulfonamide-7,7 dioxide Hydrochloride (I)

A mixture of compound from example 8 (15 gm0.0462 mole) and di-p-toluyl-D-tartaric acid monohydrate (4.55 gm, 0.01125 mole) in n-propanol (1600 ml) was heated to boiling and hot solution filtered through a filter-aid pad with a layer of charcoal. The filtrate was concentrated by boiling to a volume of about (400 ml) and then allowed to crystallize. After standing overnight the crystals were filtered off and material recrystallized twice more from n-propanol (400 ml) to yield a 2:1 salt of free base to acid. Combined mother liquors from this recrystallization were saved for stage B. The salt was then treated with a saturated solution of sodium bicarbonate and mid extracted with ethyl acetate. The organic extract were dried, filtered and concentrated to dryness to yield (3.2 gm) of freebase. The hydrochloride salt was prepared from 5,6 N HCl ethanol and crystallized from methanol-isopropanol to yield (2.83 gm) of (+) isomer, SOR 8.23 (C 0.9 methanol) M.P. 283–285° C. The combine mother liquor was treated with saturated solution of sodium bicarbonate and mixture extracted with ethyl acetate. The organic exacts were dried, filtered and concentrated to dryness. The residue was treated with di-p-toluyl-L-tartaric acid monohydrate (4.55 gm, 0.01125 mole) in n-propanol (1600 ml) and the isomer separated by the process described previously to give title compound (I) (3.75 gm, 22.48%) SOR=−8.34 (C 1, Methanol) M.P. 283 to 285° C.

We claim:

1. A process for preparing 5,6-dihydro-4-(S)-(ethylamino)-6-(S)methyl-4H-thieno[2,3b]thiopyran-2-sulphonamide-7,7-dioxide hydrochloride of formula (I),

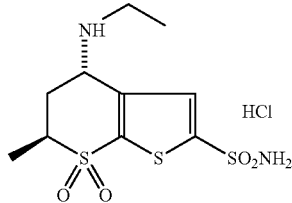
(I)

the process comprising
(a) reacting compound of formula II wherein X is halo, with magnesium metal and treating the generated Grignard reagent in a solvent in situ with sulfur, triethyl amine hydrochloride, crotonic acid and suitable base to obtain compound of formula III,

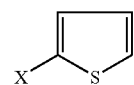
II

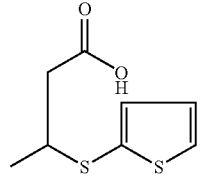
III (b) reacting compound of formula III with a chlorinating agent to obtain a acid chloride, followed by subjecting the acid chloride to cyclisation in the presence of a Lewis acid to obtain a compound of formula IV;

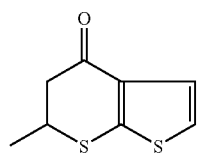
IV (c) reacting compound of formula IV with a mixture of chlorosulphonic acid and a chlorinating agent to form a sulphonylchloride of formula XX, extracting the sulphonylchloride in a chlorinated solvent, washing with water, drying and evaporating the chlorinated solvent to obtain compound of formula V;

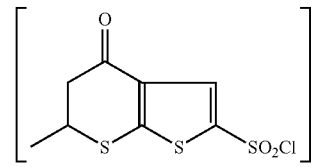
XX

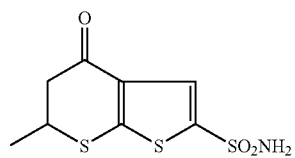
V (d) reducing compound of formula V to obtain compound of formula VI;

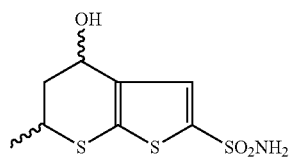
VI (e) oxidising compound of formula VI to obtain compound of formula VII;

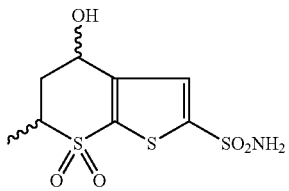
VII (f) subjecting compound of formula VII to a Ritter reaction to obtain compound of formula VIII

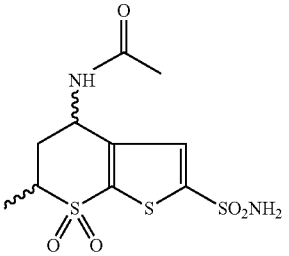
VIII (g) reducing compound of formula VIII to obtain compound of formula IX

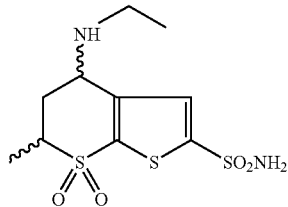

IX (h) converting compound of formula IX to acid addition salt thereof of formula XXI and recrystallizing enriched salt from the solvent and then converting salt of formula XXI to compound of formula X

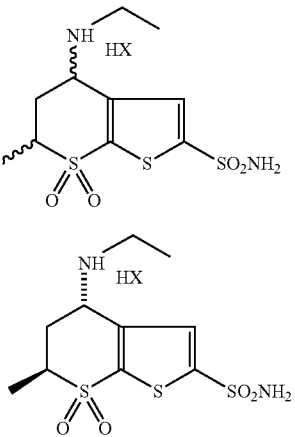

XXI

X (i) resolving compound of formula X into compound of formula I.

2. A process as claimed in claim 1 wherein in step (a), the organic solvent is selected from the group consisting of ethers, cyclic ethers and aromatic hydrocarbon.

3. A process as claimed in claim 1 wherein the organic solvent used in step (a) is tetrahydrofuran.

4. A process as claimed in claim 1 wherein step (a) is carried out in the presence of a base selected from the group consisting of organic alkylamine and pyridine.

5. A process as claimed in claim 1 wherein the base is trialkyl amine.

6. A process as claimed in claim 1 wherein the base is triethyl amine.

7. A process as claimed in claim 1 wherein in compound of formula II, X is a halo selected from the group consisting of Cl, Br and I.

8. A process as claimed in claim 1 wherein step (a) is carried out at a temperature in the range of 0° C. to 70° C.

9. A process as claimed in claim 1 wherein in step (b), the organic solvent is an aprotic non-polar solvent.

10. A process as claimed in claim 9 wherein the aprotic non-polar solvent used is a chlorinated solvent.

11. A process as claimed in claim 10 wherein the chlorinated solvent is MDC.

12. A process as claimed in claim 1 wherein the Lewis acid used in step (b) is selected from the group consisting of $AlCl_3$, $ZnCl_2$ and $SnCl_4$.

13. A process as claimed in claim 1 wherein the Lewis acid in step (b) is $SnCl_4$.

14. A process as claimed in claim 1 wherein the sulfonyl chloride of formula XX is dissolved in step (c) in an organic solvent selected from the group consisting of ether and ketone.

15. A process as claimed in claim 1 used in step (c) wherein the organic solvent is tetrahydrofuran.

16. A process as claimed in claim 1 wherein in step (c) the sulfonyl chloride of formula XX is dissolved in an organic sovlent and then treated with ammonia followed by chlorination with a chlorinating agent selected from the group consisting of $POCl_3$, $PCl_5$, $PCl_3$ and $SOCl_2$ and in the presence of a chlorination solvent selected from the group consisting of $CHCl_3$, MDC, and EDC.

17. A process as claimed in claim 16 wherein the chlorinating agent is $SOCl_2$.

18. A process as claimed in claim 16 wherein the chlorination solvent is MDC.

19. A process as claimed in claim 1 wherein in step (d) reduction is effected using sodium borohydride in the presence of a solvent and at a temperature in the range of 0° C. to 40° C.

20. A process as claimed in claim 19 wherein the solvent is a lower aliphatic alcohol.

21. A process as claimed in claim 20 wherein the lower aliphatic alcohol is methanol.

22. A process as claimed in claim 1 wherein in step (e) compound of formula VI is oxidised with sodium perborate in presence of acetic acid at 20° C. to 70° C.

23. A process as claimed in claim 1 wherein in step (f) the Ritter reaction of compound of formula VII is effected in a strong acid with acetonitrile at 10° C. to 40° C.

24. A process as claimed in claim 23 wherein the strong acid is selected from the group consisting of sumac acid and a mixture of concentrated sulfuric acid and fuming sulfuric acid.

25. A process as claimed in claim 1 wherein in step (g), reduction is effected using borane dimethylsulfide complex in an organic solvent selected from ether and cyclic ether.

26. A process as claimed in claim 1 wherein the organic solvent used in step (g) is tetrahydrofuran.

27. A process as claimed in claim 1 wherein in step (h), the organic solvent is selected from the group consisting of a ketone, an ester, a dipolar aprotic solvent, lower aliphatic alcohol, aliphatic hydrocarbon and aromatic hydrocarbon.

28. A process as claimed in claim 27 wherein the ester is ethyl acetate.

29. A process as claimed in claim 1 wherein the acid used for salt formation in step (h) is a mineral acid selected from the group consisting of HCl, $H_2SO_4$, $HNO_3$, and HBr dissolved in a lower aliphatic alcohol.

30. A process as claimed in claim 29 wherein the acid is ethanolic HCl.

31. A process as claimed in claim 1 wherein the organic solvent used for recrystallization in step (h) is selected from the group consisting of a ketone, an ester, a dipolar aprotic solvent, lower aliphatic alcohol, aliphatic hydrocarbon and aromatic hydrocarbon.

32. A process as claimed in claim 31 wherein the organic solvent is selected from an ester, lower aliphatic alcohol and mixture thereof.

33. A process as claimed in claim 32 wherein the organic solvent is selected from ethyl acetate, ethanol and mixture thereof.

34. A process as claimed in claim 1 wherein the compound of formula X is resolved using di-p-toluyl-tartarate and di-p-toluyl-D-tartarate.

* * * * *